(12) United States Patent
Heacock

(10) Patent No.: US 9,746,421 B2
(45) Date of Patent: Aug. 29, 2017

(54) APPARATUSES, INDICATORS, METHODS AND KITS WITH TIMED COLOR CHANGE INDICATION

(71) Applicant: Gregory Heacock, Maple Valley, WA (US)

(72) Inventor: Gregory Heacock, Maple Valley, WA (US)

(73) Assignee: Sensor International, LLC, Maple Valley, WA (US)

( * ) Notice: Subject to any disclaimer, the term of this patent is extended or adjusted under 35 U.S.C. 154(b) by 0 days.

(21) Appl. No.: 14/038,586

(22) Filed: Sep. 26, 2013

(65) Prior Publication Data
US 2015/0087076 A1    Mar. 26, 2015

(51) Int. Cl.
*B01L 3/00*    (2006.01)
*G01N 21/78*    (2006.01)
*G01N 31/22*    (2006.01)

(52) U.S. Cl.
CPC .......... *G01N 21/78* (2013.01); *G01N 31/229* (2013.01); *G01N 21/783* (2013.01)

(58) Field of Classification Search
CPC .. B01L 3/502715; G01N 33/02; G01N 21/78; G01N 2021/775
See application file for complete search history.

(56) References Cited

U.S. PATENT DOCUMENTS

| | | |
|---|---|---|
| 3,018,611 A | 1/1962 | Biritz |
| 2,768,976 A | 10/1973 | Hu |
| 3,899,295 A | 8/1975 | Halpern |

(Continued)

FOREIGN PATENT DOCUMENTS

| | | |
|---|---|---|
| CN | 101479584 | 7/2009 |
| CN | 101501468 | 8/2009 |

(Continued)

OTHER PUBLICATIONS

International Preliminary Report on Patentability in PCT/US2012/063797, dated Jun. 19, 2014 (10 pages).

(Continued)

*Primary Examiner* — Dennis M White
(74) *Attorney, Agent, or Firm* — McAndrews, Held and Malloy

(57) ABSTRACT

An apparatus, method and kit includes one or more use protocol indicators having a color changeable dye, the dye being translucent or having a first color upon immediate exposure to an environment and for a defined time thereafter and the dye changing color after exposure to the environment for the defined time. A dual environment indicator includes a first indicator color changeable dye being translucent or having a first color upon immediate exposure to a first environment and changing color after exposure to a second environment and a second indicator color changeable dye being translucent or having a first color upon immediate exposure to the second environment and for a defined time thereafter and changing color after exposure to the second environment for the defined time. A time exposure indicator comprises at least one color changeable dye disposed to change color in a sequential manner.

22 Claims, 16 Drawing Sheets
(12 of 16 Drawing Sheet(s) Filed in Color)

(56) References Cited

U.S. PATENT DOCUMENTS

| | | | |
|---|---|---|---|
| 3,939,968 | A | 2/1976 | Ryder |
| 4,003,709 | A | 1/1977 | Eaton |
| 4,098,577 | A | 7/1978 | Halpern |
| 4,135,792 | A | 1/1979 | Deeg et al. |
| 4,526,752 | A | 7/1985 | Perlman et al. |
| 5,159,360 | A | 10/1992 | Stoy et al. |
| 5,518,927 | A | 5/1996 | Malchesky et al. |
| 5,623,323 | A | 4/1997 | Johnosn et al. |
| 5,706,073 | A | 1/1998 | Volk |
| 5,942,438 | A | 8/1999 | Antonoplos et al. |
| 6,060,210 | A | 5/2000 | Eda et al. |
| 6,114,509 | A | 9/2000 | Olsen et al. |
| 6,132,086 | A | 10/2000 | Henwood |
| 6,218,189 | B1 | 4/2001 | Antonoplos et al. |
| 6,254,969 | B1 | 7/2001 | Eberle |
| 6,270,724 | B1 | 8/2001 | Woodman |
| 6,518,231 | B2 | 2/2003 | Appel et al. |
| 6,634,747 | B1 | 10/2003 | Atkins et al. |
| 6,634,753 | B1 | 10/2003 | Rozeman |
| 6,710,221 | B1 | 3/2004 | Pierce et al. |
| 6,790,411 | B1 | 9/2004 | Read |
| 6,851,808 | B2 | 2/2005 | Heacock |
| 7,219,799 | B2 | 5/2007 | Bonnette et al. |
| 7,244,252 | B2 | 7/2007 | Berndt |
| 7,785,299 | B2 | 8/2010 | Crawford et al. |
| 8,137,303 | B2 | 3/2012 | Crawford et al. |
| 8,163,237 | B2 | 4/2012 | Crawford et al. |
| 8,257,663 | B2 | 9/2012 | Crawford et al. |
| 8,338,131 | B2 | 12/2012 | Callen et al. |
| 8,388,131 | B2 | 3/2013 | Heacock |
| 8,663,998 | B2 | 3/2014 | Heacock |
| 2002/0022008 | A1 | 2/2002 | Forest et al. |
| 2002/0023642 | A1 | 2/2002 | Allard et al. |
| 2002/0137123 | A1 | 9/2002 | Hui |
| 2003/0199095 | A1 | 10/2003 | Yuyama et al. |
| 2004/0115319 | A1 | 6/2004 | Morris |
| 2004/0180391 | A1 | 9/2004 | Gratzl et al. |
| 2005/0041200 | A1 | 2/2005 | Rich |
| 2005/0125924 | A1 | 6/2005 | Benjamin et al. |
| 2005/0164898 | A1 | 7/2005 | Katsuri et al. |
| 2006/0046301 | A1 | 3/2006 | Happe |
| 2006/0054525 | A1 | 3/2006 | Dean et al. |
| 2006/0054526 | A1 | 3/2006 | Dean |
| 2006/0069305 | A1 | 3/2006 | Couvillon et al. |
| 2006/0110835 | A1 | 5/2006 | Gohil |
| 2006/0181676 | A1 | 8/2006 | Tucker et al. |
| 2007/0017042 | A1 | 1/2007 | Cincotta et al. |
| 2007/0140911 | A1 | 6/2007 | Carney et al. |
| 2008/0129960 | A1 | 6/2008 | Heacock |
| 2009/0301382 | A1 | 12/2009 | Patel |
| 2009/0303440 | A1 | 12/2009 | Heacock et al. |
| 2010/0112680 | A1* | 5/2010 | Brockwell et al. ........ 435/287.9 |
| 2011/0130727 | A1 | 6/2011 | Crawford et al. |
| 2011/0130728 | A1 | 6/2011 | McKinnon et al. |
| 2011/0259086 | A1 | 10/2011 | Harris et al. |
| 2012/0276647 | A1 | 11/2012 | Mills |
| 2013/0130399 | A1 | 5/2013 | Mills |
| 2013/0150785 | A1 | 6/2013 | Heacock |
| 2013/0269592 | A1* | 10/2013 | Heacock et al. ............. 116/206 |
| 2014/0296402 | A1 | 10/2014 | Jung et al. |
| 2015/0087076 | A1 | 3/2015 | Heacock |
| 2015/0225304 | A1 | 8/2015 | Donze et al. |

FOREIGN PATENT DOCUMENTS

| | | |
|---|---|---|
| EP | 0231499 | 8/1987 |
| EP | 2021755 | 5/2007 |
| WO | WO 02/099416 | 12/2002 |
| WO | 2004077035 | 9/2004 |
| WO | 2007/018301 | 2/2007 |
| WO | 2008095960 | 8/2008 |
| WO | 2013/085655 | 6/2013 |
| WO | 2013085655 A1 | 6/2013 |

OTHER PUBLICATIONS

Ex Parte Quayle Action in U.S. Appl. No. 12/504,107 dated Oct. 16, 2012.

Extended Supplementary European Search Report, EP Application No. EP07864168, Mar. 1, 2011.

Final Rejection in U.S. Appl. No. 11/607,298 dated Jan. 26, 2009.

International Search Report and Written Opinion of the International Searching Authority, or the Declaration, in International application No. PCT/US2012/63797, dated Jan. 17, 2013. (10 pages).

International Search Report corresponding to International Application No. PCT/US2007/84186, mailed Sep. 2, 2008, 2 pages.

Issue Notification in U.S. Appl. No. 12/504,107 dated Feb. 13, 2013.

Michael Freemantle, Intelligence Ink Detects Oxygen, Chemical Gas Sensing, Aug. 2, 2004, p. 11, vol. 82, No. 31, Chemical & Engineering News USA.

Non-Final Rejection in U.S. Appl. No. 11/607,298 dated Jul. 29, 2008.

Non-Final Rejection in U.S. Appl. No. 12/504,107 dated Mar. 28, 2012.

Non-Final Rejection in U.S. Appl. No. 13/688,550 dated Feb. 14, 2013.

Notice of Allowance in U.S. Appl. No. 12/504,107 dated Nov. 19, 2012.

Notification Concerning Transmittal of International Preliminary Report on Patentability, PCT/US2007/084186, mailed Jun. 11, 2009, 12 pages.

Requirement for Restriction/Election in U.S. Appl. No. 11/607,298 dated Mar. 18, 2008.

Requirement for Restriction/Election in U.S. Appl. No. 12/504,107 dated Oct. 26, 2011.

Requirement for Restriction/Election in U.S. Appl. No. 13/315,840 dated Sep. 12, 2013.

Swann et al., "Designing Out Curative Syringe Reuse: Maximising Global Acceptance and Impact by Design," Internet Citation, http://eprints.hud.ac.uk/11783/ [dated Sep. 18, 2013] abstract.

The Guardian, Architecture and Design Blog with Oliver Wainwright, "How colour-changing technology could revolutionise the medical industry," Internet Citation, http://www.theguardian.cco/artanddesign/architectarc-design-blog/2013/aug/28/colour-changing-syringe-medical-design [dated Sep. 18, 2013].

Written Opinion of the International Searching Authority corresponding to International Application Serial No. PCT/US2007/84186, mailed Sep. 2, 2008, 12 pages.

European Patent Office, Communication with extended European search report, in Application No. 14166858.2, dated Sep. 4, 2014 (7 pages).

PCT, Notification of Transmittal of the International Search Report and the Written Opinion of the International Searching Authority, or the Declaration, in Application No. PCT/US14/57225, dated Dec. 17, 2014 (11 pages).

European Patent Office, Communication with extended European search report in application No. 12855085.2, dated Aug. 3, 2015 (6 pages).

PCT, Notification of Transmittal of the International Search Report and the Written Opinion of the International Searching Authority, in Application No. PCT/US2015/032885, dated Aug. 14, 2015 (10 pages).

PCT, International Search Report, Application No. PCT/US2014/057225, dated Sep. 24, 2014, 2 pages.

PCT, Written Opinion ofthe International Searching Authority, Application No. PCT/US2014/057225, dated Sep. 4, 2014, 4 pages.

European Patent Office Office Action, dated May 24, 2017, re: Applicant: Sensor International, LLC, Application No. 4847026.3-1554/3049135 PCT/US2014057225 (13 pages).

* cited by examiner

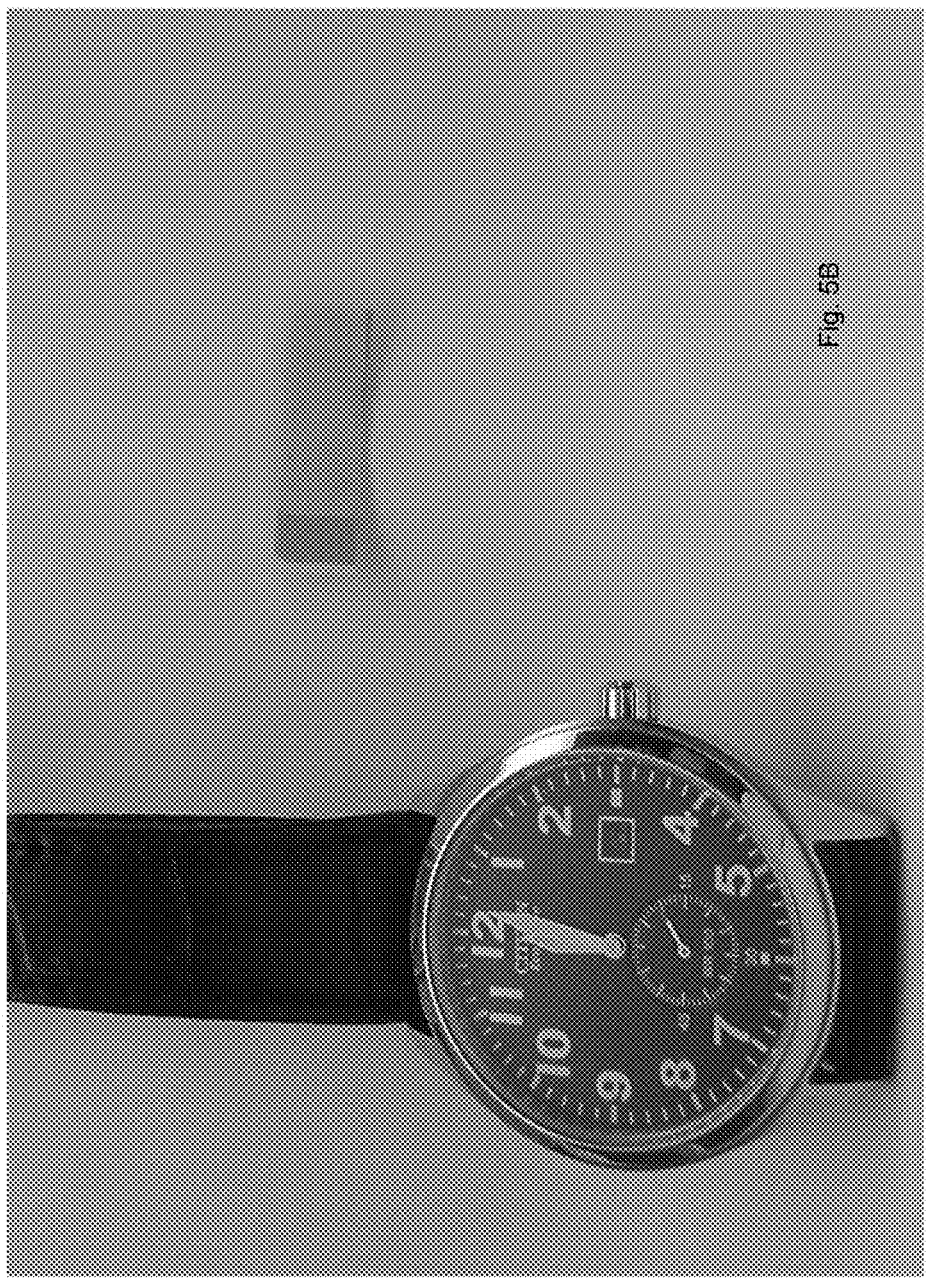

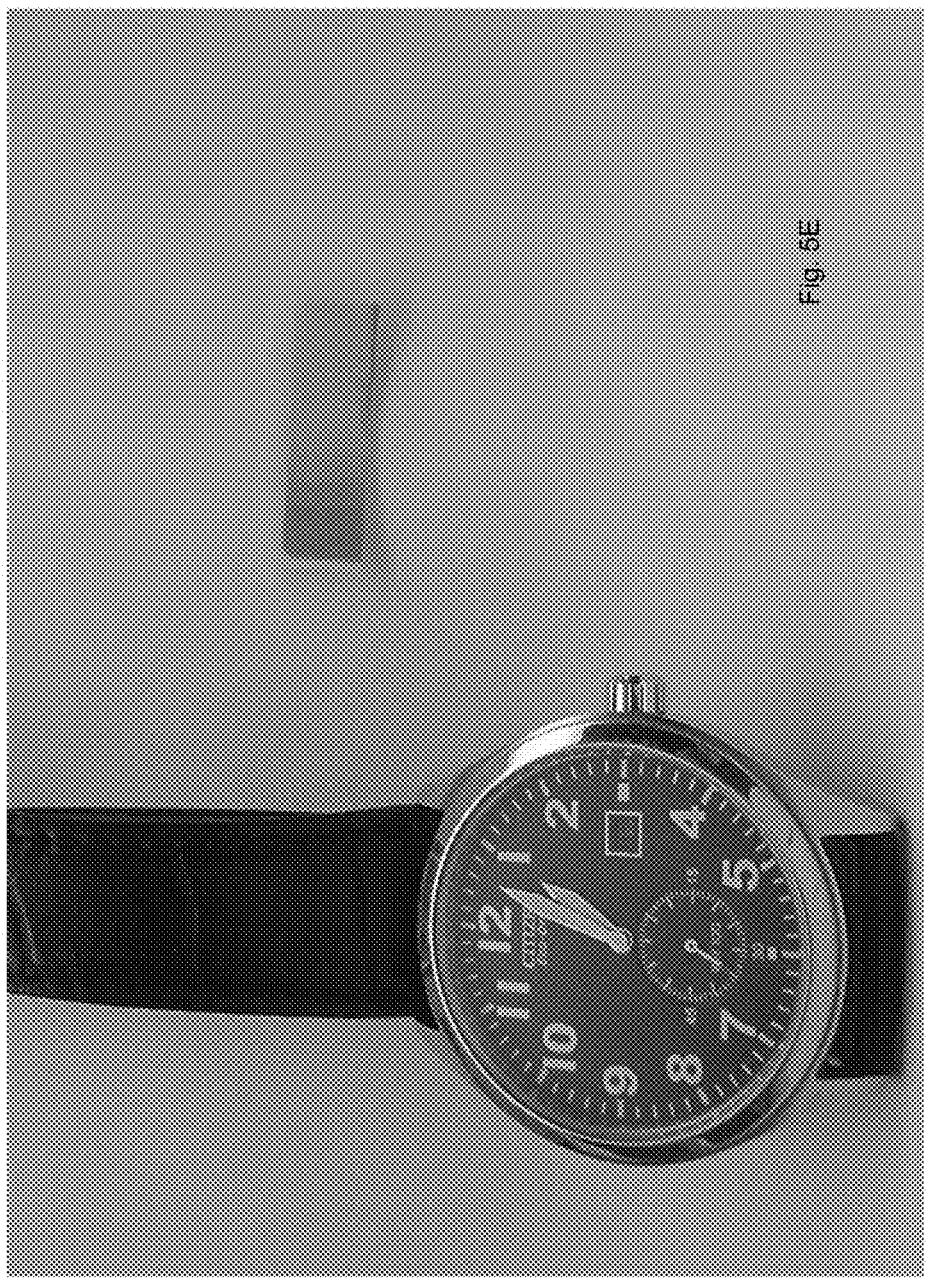

APPARATUSES, INDICATORS, METHODS AND KITS WITH TIMED COLOR CHANGE INDICATION

CROSS-REFERENCE TO RELATED APPLICATIONS

[Not Applicable]

FEDERALLY SPONSORED RESEARCH OR DEVELOPMENT

[Not Applicable]

FIELD OF THE INVENTION

Generally speaking, the present application relates to a color changeable indicator that changes color after being exposed to a particular environment for a predetermined period of time. In one embodiment, the color changeable indicator is intended for use on or in disposable, limited or restricted use products that can transmit contaminants or disease to a person, cause infection, or decline in quality or potency if reused or used beyond a recommended period of time. In another embodiment, the color changeable indicator is intended for use on or in packaging for a product for human consumption wherein the product for human consumption can decline in freshness, quality of taste, and/or potency and/or can cause disease if consumed beyond a recommended period of time. The color changeable indicator acts to indicate that a product should no longer be used or consumed.

More specifically, one embodiment of the present application relates to disposable, limited or restricted use product having multiple use protocols which affect the lifespan of the product. The present application deals with use protocol indicators having a color changeable dye that changes color after exposure to a particular environment for a defined time. The defined time corresponds to, for example, the expiration time for a disposable, limited or restricted use product for a particular protocol(s) or the time after which a product should no longer be used or consumed.

More specifically, another embodiment of the present application relates to an exposure time indicator that uses a color changeable dye or multiple color changeable dyes that change color after exposure to an environment in a sequential manner. The exposure time indicator creates a spectrum that allows the user to see how much of the product's useful life has been used and how much remains.

BACKGROUND OF THE INVENTION

Many products currently marketed and sold to consumers are designed for limited use. These products are usually associated with a single event, a restricted time period or restricted access. There are many reasons for the need of single use or limited use products.

An example of a single use product is a disposable syringe. Instrument contamination and cross infection between patients is an ever present concern if the syringe is inadvertently reused. It is a particular concern in some countries where repeated use of instruments is known to transmit serious diseases such as HIV and hepatitis. Medical and ophthalmic devices that must be sterilized such as scalpels or tonometers (for the measurement of a patient's intraocular pressure) and body piercing and tattooing instruments used on multiple clients also give cause for concern. Needles used in acupuncture offer another example. Decontamination procedures or employment of single-use devices are methods used to control cross infection, but they rely on personnel awareness, willingness to follow protocol, monitoring and documentation.

The limited use type of product is usually associated with goods that should be used for a restricted time period. One example of this type of product is "daily wear" or disposable contact lenses. Contact lenses for refractive correction or cosmetic purposes require suitable wear and care regimes in order to maintain good eye health. Non-compliance on the part of the patient, either through choice or due to lack of education, can injure the eye. Frequent replacement lenses are sometimes worn for longer than recommended or they may be stored or cleaned inappropriately.

Other examples of limited use products that have a shelf life after which they should not be used because of a risk of infection or a decrease in effectiveness are cosmetic products, personal hygiene products such as electric toothbrush heads, and home diagnostic kits such as pregnancy tests and ovulation prediction tests. For example, it has been found that cosmetic applicators can harbor bacteria that can infect the eye and should be disposed of prior to their expiration to prevent eye infections.

Many products currently marketed and sold to consumers are supplied prepackaged where the packaging is intended to preserve the freshness of the product such as food or beverages or in the case of medication, the potency of the content within the packaging. These products are usually associated with a single event, i.e., the contents remain fresh or potent until the packaging is opened by the consumer; however, the freshness or quality of the contents may decrease over time.

An example of the importance of preservation of a packaged product is a cold tablet or a food item. Medicinal potency or food spoilage and the expense related to these issues are important to both consumers and manufacturers. Pharmaceuticals, food stuff, and similar items are commonly packaged in sealed plastic containers.

Gas, such as oxygen, permeation through the plastic material of the container negatively affects the freshness or quality of the contents of many packaged products. In the case of pharmaceuticals, oxygen absorption decreases potency. In the case of food products, oxygen absorption into the packaged food makes the food taste stale.

Products may have different intended uses and may have different times after which the product should no longer be used based on the intended use. For example, a single medical device could have many different use protocols. Depending on the use protocol, the medical device should be changed after a different period of time. For example, a catheter could be used in one way where it should be changed after 72 hours but when used another way would not need to be changed until 96 or 168 hours. Medications could also have a different shelf life based on different uses. For example, maximum potency might be required for a certain use while a decline in potency would be acceptable for an alternate use. Foods could similarly have a different shelf life based on their intended use. The same food product might be deemed acceptable for consumption by a pet longer than it would be deemed acceptable for consumption by a human.

BRIEF SUMMARY OF THE INVENTION

The present application relates to a color changeable dye that changes color after being exposed to a particular environment for a predetermined period of time.

In one embodiment of the present application, an apparatus with color change indication comprises a disposable, limited or restricted use product having more than one use protocol and at least one interchangeable use protocol indicator having a color changeable dye, the dye being translucent or having a first color upon immediate exposure to an environment and for a defined time thereafter and the dye changing color after exposure to the environment for the defined time.

The environment can be an oxygen containing environment and said color changeable dye is an oxygen sensing color changeable dye. The environment can be a carbon dioxide containing environment and said color changeable dye can be a carbon dioxide sensing color changeable dye. The environment can be a carbon dioxide containing environment and said color changeable dye can be an oxygen sensing color changeable dye.

The at least one interchangeable use protocol indicator can be incorporated into the disposable, limited or restricted use product. For example, the at least one interchangeable use protocol indicator cab have a capillary with the color changeable dye incorporated therein. The at least one interchangeable use protocol indicator can be disposed on the disposable, limited or restricted use product. The at least one use protocol indicator can be provided with the disposable, limited or restricted use product.

The at least one interchangeable use protocol indicator can be an exposure time indicator.

In another embodiment of the present application, an apparatus having a color change indicator comprises a first indicator color changeable dye, the dye being translucent or having a first color upon immediate exposure to a first environment and the dye changing color after exposure to a second environment; and a second indicator color changeable dye, the dye being translucent or having a first color upon immediate exposure to the second environment and for a defined time thereafter and the dye changing color after exposure to the second environment for the defined time. The first environment can be carbon dioxide or inert gas and the second environment can be atmospheric oxygen. The indicator can be an exposure time indicator.

In yet another embodiment of the invention, an apparatus with color change indication comprises an exposure time indicator comprising at least one color changeable dye, wherein the at least one color changeable dye is disposed to change color in a sequential manner. The at least one color changeable dye can be translucent or have a first color upon immediate exposure to an environment and change color after exposure to the environment. The exposure time indicator can have a first region of the color changeable dye changes color after a first time, consecutive regions of the color changeable dye change color at increasing time intervals after the first time and a final region changes color after a final defined time. The final defined time can correspond to an expiration time for a disposable, limited or restricted use product.

The environment can be an oxygen containing environment and said color changeable dye can be an oxygen sensing color changeable dye. The environment can be a carbon dioxide containing environment and said color changeable dye can be a carbon dioxide sensing color changeable dye.

The exposure time indicator can be incorporated into a disposable, limited or restricted use product. For example, the exposure time indicator can be a capillary with the color changeable dye incorporated therein. The exposure time indicator can be disposed on a disposable, limited or restricted use product.

The exposure time indicator can have barrier layers over the regions of color changeable dye to achieve the sequential color change.

In yet another embodiment of the present application, a method of using an apparatus with color change indication comprises providing a disposable, limited or restricted use product having more than one use protocol said more than one use protocols having an associated use protocol indicator with a color changeable dye, the dye being translucent or having a first color upon immediate exposure to an environment and for a defined time thereafter and the dye changing color after exposure to the environment for the defined time; and selecting at least one use protocol indicator.

In yet another embodiment of the present invention, a kit comprises more than one use protocol indicator having a color changeable dye, the dye being translucent or having a first color upon immediate exposure to an environment and for a defined time thereafter and the dye changing color after exposure to the environment for the defined time wherein said more than one use protocol indicators have different defined times. The kit further can include a disposable, limited or restricted use product. The use protocol indicators can be adhesive use protocol indicators.

These and other advantages and novel features of the present invention, as well as details of illustrated embodiments thereof will be more fully understood from the following description of the drawings.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 5A-5L are photographs of an exposure time indicator with a color changeable dye that changes color after exposure to an environment in a sequential manner.

Figure 1:
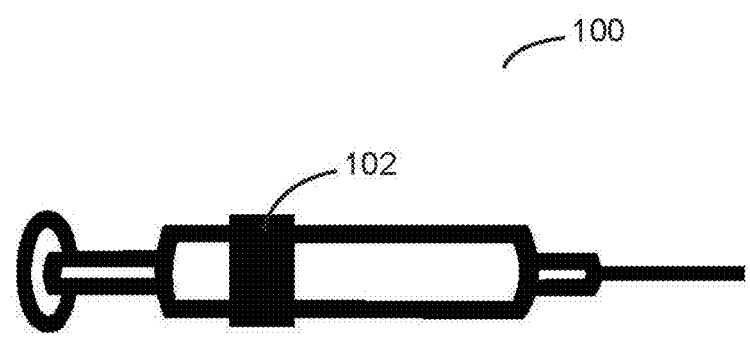
FIG. 1 is a schematic drawing of one embodiment of the present invention showing a medical device having an interchangeable use protocol indicator incorporated therein.

The foregoing summary, as well as the following detailed description of certain embodiments of the present application, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE INVENTION

In accordance with the present invention, a color change indication on a product provides accurate information or a warning to a user of: prior use of a single use product or instrument; a reminder that a limited use product has reached its expiration time; or that a product that is restricted for use has been tampered with. The warning indication is provided by a dye that changes color in a time controlled manner. The dye can be disposed on the product itself by being either printed on the product or incorporated into the product or within the material forming a portion of the product. The dye can also be disposed on or incorporated into a packaging or other article that accompanies the product. The product is then subsequently packaged to provide a sterile environment for the product or limited access thereto. The internal atmosphere of the package is an inert gas, carbon dioxide, or a vacuum such that the package provides a sealed environment free of substances that trigger the color change of the dye, such as oxygen, carbon dioxide, nitrogen, water, etc. When the package is subsequently opened and the product is exposed to a trigger substance, such as atmospheric oxygen, the dye disposed on the product will change from a first color (often translucent or somewhat translucent, i.e. a milky white or "water white") to a second color (often a blue or red color) after a period of time that is controlled by the composition of the dye and other factors as discussed in detail below, and that is selected to correspond to the typical time for a single use of a product in the case of single use products or that corresponds to the expiration time of the product. The time at which the dye changes color can also be selected so as to indicate that the product may have been tampered with.

Prior patents and applications co-owned by applicant have dealt with the use of color changeable dyes. U.S. Pat. No. 8,388,131 presented a disposable limited or restricted use apparatus that includes a color changeable portion wherein the time that the color change occurs is controlled so that it coincides to the approximate time of the end of one use of a single use apparatus or to the approximate expiration time for extended but limited or restricted use apparatus. U.S. Pub. No. 2013/0150785 presented a color changeable dye including a redox indicator to create a color change indication on a product that provides accurate information or a warning to a user of, e.g.: prior use of a single use product or instrument; a reminder that a limited use product has reached its expiration time; or that a product that is restricted for use has been tampered with. U.S. Pat. No. 8,388,131 and its related cases (e.g. U.S. Pub. No. 2013/0088683, U.S. application Ser. Nos. 13/780,050 and 13/795,343) and U.S. Pub. No. 2013/0150785 are incorporated herein in their entirety by reference.

The present application further addresses disposable, limited or restricted use products with multiple use protocols. For example, a medical device such as a catheter may have multiple different procedures for which it can be used. The time after which the medical device reaches its expiration may be different depending on the procedure for which it is being used. For example, a connector or adapter may be used in one use protocol in conjunction with a medical device delivering oncology medication where the device should only be used for a single dose, e.g., around six hours. The connector or adapter could alternatively be used in a second use protocol with a catheter that delivers drugs for an infection over a period 96 hours. The connector or adapter could alternatively be used in a third use protocol with a medical device that delivers insulin therapy to a patient over 168 hours. The present application offers a use protocol indicator that utilizes a color changeable dye to indicate the time after which a disposable, limited or restricted use product should no longer be used for a specific use protocol. In such an embodiment, an apparatus with color change indication comprises a disposable, limited or restricted use product and at least one interchangeable use protocol indicator.

The disposable, limited or restricted use product has at least one use protocol. More commonly, the disposable, limited or restricted use product has more than one use protocol. For example, a disposable, limited or restricted use product could have 2, 3, 4, 5, 6, 7, 8, 9, 10, 11, 12, 13, 14, 15, 16, 17, 18, 19, 20, 21, 22, 23, 24, 25, or more use protocols. Each use protocol has a defined time after which the disposable, limited or restricted use product should not be used when it has been used for that particular use protocol. For example, the medical device could have one use protocol for which it should not be used after exposure to oxygen for 72 hours, it could have a second use protocol after which it should not be used after exposure to oxygen for 96 hours, a third use protocol after which it should not be used after exposure to oxygen for 168 hours and a fourth use protocol after which it should not be used after a week. As another example, the medical device could have one use protocol for which it should not be used after exposure to oxygen for 6 hours, it could have a second use protocol after which it should not be used after exposure to oxygen for 12 hours, a third use protocol after which it should not be used after exposure to oxygen for 90 hours and a fourth after which it should not be used after 120 hours.

The interchangeable use protocol indicator has a color changeable dye. The color changeable dye is translucent, water white or a first color upon immediate exposure to an environment and for a defined time thereafter. The dye changes color after exposure to the environment for the defined time which corresponds to a time after which the disposable, limited or restricted use product should not be used for a particular use protocol. Where there are multiple use protocols for the disposable, limited or restricted use product there can be multiple interchangeable use protocol indicators. The indicator may be interchangeable such that a single indicator is adapted such that it may be used with multiple different products or different indicators can be used with a single product. The multiple use protocol indicators can have color changeable dyes such that the defined time after which the color changeable dyes change corresponds to the expiration time for the disposable, limited or restricted use product for a particular use protocol. For example, the medical device discussed above with use protocols for which it should not be used after exposure to oxygen for 72 hours, 96 hours and 168 hours could have three use protocol indicators with color changeable dyes that change after exposure to oxygen for 72 hours, 96 hours and 168 hours respectively. The expiration time for a disposable, limited or restricted use product can be the time after which the manufacturer recommends replacement, the time after which the product will decline in quality, potency or effectiveness and/or the time after which the product could be dangerous to use.

The color changeable dye can be varied in order to change color in response to a variety of different environments for a defined time. In a preferred embodiment, the environment is an oxygen containing environment and the color changeable dye is an oxygen (O2) sensing color changeable dye. In another preferred embodiment, the environment is a carbon dioxide containing environment and the color changeable dye is a carbon dioxide (CO2) sensing color changeable dye. In another preferred embodiment, the indicator with an oxygen or carbon dioxide sensing color changeable dye is contained within a carbon dioxide rich environment and later exposed to an atmospheric oxygen environment. In another preferred embodiment, the indicator with a carbon dioxide sensing color changeable dye is contained within an oxygen rich environment and later exposed to a carbon dioxide rich environment. In another preferred embodiment, the indicator with an oxygen or carbon dioxide sensing color changeable dye is contained within an inert gas environment and later exposed to an atmospheric oxygen or carbon dioxide environment. The environment to which the color changeable dye responds can be chosen based on the particular use protocol. For example, a medical device could have one use protocol for which it should not be used after exposure to oxygen for 1 hour, it could have a second use protocol after which it should not be used after exposure to oxygen for 8 hours and a third use protocol after which it should not be used after exposure to carbon dioxide for 20 minutes. The color changeable dye for the associated interchangeable use protocol indicators could be selected accordingly such that the color changeable dyes on the three use protocol indicators change after exposure to oxygen for 1 hour, exposure to oxygen for 8 hours and exposure to carbon dioxide for 20 minutes respectively.

The color change indicator may include a first indicator color changeable dye, the dye being translucent or having a first color upon immediate exposure to a first environment (such as carbon dioxide or inert gas) and the dye changing color after exposure to a second environment (such as atmospheric oxygen); and a second indicator color changeable dye the dye being translucent or having a first color upon immediate exposure to the second environment and for a defined time thereafter and the dye changing color after exposure to the second environment for the defined time. As one embodiment, an indicator may include a first indicator dye and a second indicator dye such that the first indicator dye indicates a packaging condition and the second indicator dye is associated with a use protocol. For example, an indicator may include a carbon dioxide sensing dye and an oxygen sensing dye where the indicator is packaged within in a carbon dioxide rich environment which triggers the carbon dioxide sensing dye, indicating that the package is sealed. When the indicator is subsequently removed from the package, the oxygen sensing dye will serve as a use protocol indicator in accordance with the present invention. Moreover, the indicator may be an exposure time indicator as described below.

In order to create dyes that change color after exposure to different environments after different periods of time there are a number of possible approaches. Dyes that have completely different compositions can be used. Variations in the makeup of the dye can be used. Scavengers, such as oxygen scavengers, can be added. Chemical or physical barriers can be also be added. Some examples of color changeable dyes using these approaches to achieve color change at different times or in response to different atmospheres are discussed below.

Examples of oxygen sensing color changeable dyes with various times of color change are discussed in U.S. Pat. No. 8,388,131 and its related cases (e.g. U.S. Pub. No. 2013/0088683, U.S. application Ser. No. 13/780,050 and U.S. application Ser. No. 13/795,343). For applications where the dye is required to be substantially translucent and wherein the dye is to change color after exposure to atmospheric oxygen after approximately 5-10 minutes, the dye solution may be formed as follows. Approximately 12 grams of glucose is added to 600 cc of distilled de-ionized water. Next, approximately 12 grams of sodium hydroxide is added to the mixture. To this mixture is added 10 cc of a Methylene Blue solution prepared by mixing 0.1 gram of Methylene Blue in 100 cc of ethanol where the ethanol evaporates in the drying process. Thereafter, 60 grams of methyl cellulose is added to the mixture. Alternatively, E414 acacia gum may be substituted for the methyl cellulose. This dye solution will change from translucent to blue in a short amount of time after the packaging is opened and the product on which the dye is disposed is exposed to oxygen. If the color change desired is from substantially translucent to a red color, 10 cc of a Safranine T solution can be substituted for the Methylene Blue solution. The Safranine T solution is prepared by mixing 0.3 grams of Safranine T with 10 ml of ethanol.

In order to delay the time at which the dye changes color upon exposure to oxygen, Iron (II) carbonate can be added to the above dye solution. For example, 0.1 grams of Iron (II) carbonate can be added to a 3 ml quantity of the above dye solution forms a dye that will change color to either blue or red after approximately 9-10 minutes of exposure to atmospheric oxygen. By increasing or decreasing the amount of Iron (II) carbonate the time that it takes for the color change to occur upon exposure to oxygen can be respectively increased or decreased. It is noted that, the addition of the Iron (II) carbonate will change the dye from being substantially translucent to somewhat translucent or a faint, milky white known as "water white" wherein the translucency diminishes as more Iron (II) carbonate is added.

If it is desired that the color change takes substantially longer than 10 minutes at atmospheric oxygen, for example, 12-16 hours at atmospheric oxygen, 0.5 grams of Iron (II) carbonate is added to a 3 ml quantity of the dye solution instead of 0.1 grams of Iron (II) carbonate. It is noted that the Iron (II) carbonate acts as an oxygen scavenger in the dye solution that preferentially absorbs oxygen, converting to Iron (III) carbonate. When the Iron (II) carbonate is completely converted to Iron (III) carbonate, the oxygen in the environment reacts with the color changeable dye so that the dye changes to blue or red and becomes visible.

In order to prevent the dye from changing color until an even longer time has passed, wax can be added to the dye solution. To provide a color change indication on a product after approximately 1500 hours at atmospheric oxygen, the oxygen diffusion rate through the dye solution can be lowered or decreased by the addition of wax as follows. Specifically, when 0.3 cc of beeswax is added to a 3 ml quantity of the dye described above, the color change is delayed by approximately ten hours at atmospheric oxygen for a volume of dye of 0.01 mm3. This amount of dye can be used in an area of approximately 2 mm in height and 20 mm long on a product. With the addition of 0.6 cc beeswax to the dye solution, the color change can be delayed to approximately 100 hours at atmospheric oxygen. To further extend the time that it takes for the color change to approximately 1500 hours at atmospheric oxygen, 0.7 grams of Iron (II) carbonate can be added to the dye solution and wax mixture.

Examples of color changeable dyes including dyes incorporating redox indicators are discussed in U.S. Pub. No. 2013/0150785. That application discusses a color changeable dye of the that may include a redox indicator, a reduction reaction initiator, an electron donor, oxygen scavenger, an indicator barrier agent, an agent to facilitate mixing and a thickening agent wherein the color changeable dye changes to a warning color after exposure to oxygen for a predetermined period.

Potential redox indicators discussed in that application include indigo tetrasulfonate, phenosafranine, methylene blue, diphenylamine, 4'-ethoxy-2,4-diaminoazobenzene, diphenylamine sulfonic acid, diphenylbenzidine sulfonic acid, tris(2,2'-bipyridine)iron, tris(1,10-phenanthroline) iron (ferrion), tris(5-nitro-1,10-phenanthroline) iron and tris(2,2'-bipyridine) ruthenium. The preferred redox indicator discussed in that application is indigo tetrasulfonate (ITS).

A reduction reaction initiator initiates the reduction of the redox indicator. An example of a reduction reaction initiator is titanium dioxide. An electron donor donates electrons to the reduction reaction initiator to allow for reduction of the redox indicator. Examples of electron donors include glycerol and sugars. In a preferred embodiment the reduction reaction initiator is titanium dioxide and the electron donor is glycerol.

Oxygen scavengers act to delay the oxidization of the redox indicator by reacting with oxygen before allowing the oxygen to react with the redox indicator. Examples of oxygen scavengers include sodium bisulfate, ascorbic acid, iron (II) carbonate. Preferred oxygen scavengers are sodium bisulfate, ascorbic acid and iron (II) carbonate.

An indicator barrier agent acts to further delay the oxidization of the redox indicator by forming a physical or chemical barrier around it. Examples of indicator barrier agents include waxes that form a physical barrier around the redox indicator and polymers that encapsulate the redox indicator. A preferred indicator barrier agent is the polymer poly(diallydimethylammonium chloride) also known as PDADMA. PDADMA acts to create a nanoreactor in the color changeable dye.

Other agents can be added to the color changeable dye in order to give the dye physical properties that make it usable for its intended purpose. For example, a thickening agent can be added to the dye to give it a workable consistency. A preferred thickening agent is 2-hydroxyethyl cellulose.

As another example of an agent that gives the dye physical properties that make it usable for its intended purpose, an agent to facilitate mixing lessens the tacky nature of the redox indicator and creates microspheres to help the hygroscopic glycerol mix with an aqueous solvent and form a usable solution. Examples of agents to facilitate mixing include bentonite nanoclay, glass microspheres and cellulose acetate. A preferred agent to facilitate mixing is bentonite nanoclay.

An example of a color changeable dye that reacts based on carbon dioxide levels in its environment could include a carbon dioxide reactive dye such as cresol red (CR, o-cresolsulfonephthalein) example formulation of 1: cresol red, 20: glycerol, 3: 10M KOH (aq), Texas red hydrazide (THR), bromothymol blue (BTB, hydroxy triarylmethane), or m-cresol purple (MCP, hydroxyl triarylmethane). This carbon dioxide reactive dye could be mixed with a solvent such as alcohol, methanol or acetone. Bentonite nanoclay or diatomaceous earth could be added to give the color changeable dye desirable physical properties.

The carbon dioxide sensing color changeable dye could then be applied to a substrate. Examples of possible substrates include a sintered material comprised of plastic, metal or other such material, a hydroxyethyl-methacrylate substrate such as that used for hydrophilic contact lenses (daily wear disposables) or a sponge that has been extruded into a filament or a strip and then dipped into the carbon dioxide color changeable dye.

The substrate with the carbon dioxide sensing color changeable dye thereon could then be laminated or encapsulated under a carbon dioxide controlled atmosphere (inclusion of or exclusion of carbon dioxide) between layers of plastic material such as Poly(vinyl chloride), (PVC), Polyethylene terephthalate (PET), or Saran having very low atmospheric diffusion rates; thus forming an indicator strip. Additionally an adhesive back could be applied to the strip to form a sticker type indicator. Under a carbon dioxide controlled atmosphere, the top of the indicator strip would be trimmed or cut off, thus presenting a small atmospheric aperture to the extruded filament or strip.

The indicator strip could then be placed onto, within or around any device or into a package. The package would preferably be flood filled with carbon dioxide. The package would be closed/sealed. Once the package was opened the indicator strip would be exposed to a low carbon dioxide environment. This would trigger the indication of the carbon dioxide sensing color changeable dye through the indicator substrate.

The indication timing control could be adjusted by adjusting the rate of carbon dioxide diffusion out of the indicator substrate, by decreasing the diameter of the aperture thus lengthening the time of the indication, or by making the strip assembly longer. A combination of adjustments such as length and aperture could also be used.

The interchangeable use protocol indicator can be provided in a number of different ways. In one embodiment, the use protocol indicator(s) can be incorporated into the disposable, limited or restricted use product itself. An interchangeable use protocol indicator that is incorporated into a product can be combined, inserted, joined or otherwise fixed into the disposable, limited or restricted use product itself (e.g., by the manufacturer or the end user). In another, embodiment the use protocol indicator(s) can be disposed on the disposable, limited or restricted use product. An interchangeable use protocol indicator that is disposed on a product is attached, affixed, adhered or otherwise fixed upon the disposable, limited or restricted use product itself (e.g., by the manufacturer or the end user).

In yet another, embodiment the use protocol indicator(s) can provided with but separate from the disposable, limited or restricted use product. In this last example, more than one use protocol indicator can be provided allowing a user to select an appropriate use protocol indicator for an intended use protocol. For example, different use protocol indicators could be provided in the packaging for a disposable, restricted or limited use medical device such as a feeding tube, catheter or connectors. The multiple use protocol indicators could be provided in the form of adhesive use protocol indicators that can be disposed on the medical device or a component such as plastic component that can be snapped into the medical device. The user could then select the use protocol indicator associated with the use protocol for which he or she intends to use the medical device. That use protocol indicator could be incorporated into the medical device or disposed on the medical device. The medical device could then be used in the intended environment. The color changeable dye on the use protocol indicator would then change color at the defined time after which the medical device should no longer be used for that particular use protocol. As another example, multiple adhesive use protocol indicators could be included in a package with a medication that has a different shelf life based on different uses. The user could then select the adhesive use protocol indicator appropriate for his or her intended use and attach it to the packaging for the medication. The use protocol indicator would then change color at the time after which the medication should no longer be used for that particular intended use.

In yet another embodiment, more than one interchangeable use protocol indicators are included in a kit. The interchangeable use protocol indicators do not have to be provided with a disposable, limited or restricted use product. They can be appropriate for use with numerous disposable, limited or restricted use products. For example, a kit of adhesive interchangeable use protocol indicators, such as stickers, could be provided with different color change times, e.g., 1 day, 3 days, 5 days, one week, etc. The user could then apply the adhesive interchangeable use protocol indicators on products, e.g., food items in a refrigerator based on the best buy date. In another example, the interchangeable use protocol indicators could be elastic loops, such as rubber bands, that could be wrapped around various products. As discussed above, the use protocol indicator(s) can be incorporated into the disposable, limited or restricted use product. The use protocol indicator(s) can be a portion of the disposable, limited or restricted use product having an appearance indicative of the use protocol for which the disposable, limited or restricted use product is intended. For example, the use protocol indicator(s) can be a portion of the disposable, limited or restricted use product having a particular color associated with a particular use protocol.

In one embodiment, the color changeable dye is disposed on the use protocol indicator. The dye can be directly disposed onto the use protocol indicator. The dye can also be indirectly disposed on the use protocol indicator. For example, the color changeable dye can be disposed on an adhesive label on the use protocol indicator. In another embodiment, the color changeable dye is incorporated into the use protocol indicator itself.

FIG. 1 is a schematic drawing of one embodiment of the present invention showing a medical device 100 having a use protocol indicator 102 with a color changeable dye incorporated therein. The use protocol indicator 102 is a plastic colored, interchangeable ring indicative of the use protocol for which the medical device is intended. For example, a first color is indicative that the medical device is intended for a first use protocol, a second color is indicative that the medical device is intended for a second use protocol, and a third color is indicative that the medical device is intended for a third use protocol.

As discussed above, the medical device can be provided with the colored component(s) already incorporated into the medical device to indicate it is intended for a certain use protocol (e.g., by the manufacturer). Alternatively, multiple interchangeable colored attachable components can be provided in the packaging with the medical device for insertion, connection or attachment by the user. The components can each have a color changeable dye that changes color after an amount of time in a certain environment associated with a particular use protocol. The user can then select the component associated with the particular use protocol for which he or she intends to use the medical device.

Figure 2:
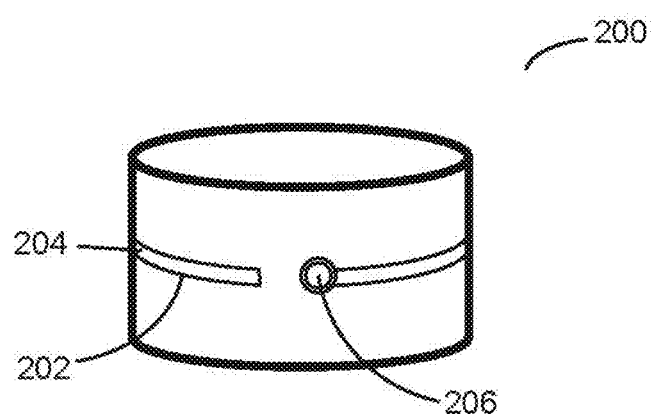
FIG. 2 is a schematic drawing of one embodiment of the present invention showing a capillary containing a color changeable dye.

As discussed above the color changeable dye can be disposed on or incorporated into the use protocol indicator. In an embodiment, a plastic colored portion is a multi-layer polymer with the color changeable dye incorporated therein. In yet another embodiment a portion has a capillary with the color changeable dye incorporated therein. FIG. 2 is a schematic drawing of one embodiment of the present invention showing an interchangeable component 200 with a capillary 202 containing a color changeable dye 204. The capillary 202 is incorporated into the interchangeable component 200. The capillary 202 can be a metal or plastic material. The capillary 202 has an aperture 206 that allows the environmental conditions to which the color changeable dye responds to access the color changeable dye 204. This controls the manner in which the environment conditions contact the color changeable dye 204. For example, where the color changeable dye 204 is an oxygen sensing color changeable dye. The aperture 206 controls the flow of oxygen to the dye. The color change of the dye can be delayed and/or controlled in this manner. Moreover, additional barrier materials may be incorporated into the capillary to further delay the color change of the dye.

Figure 3:
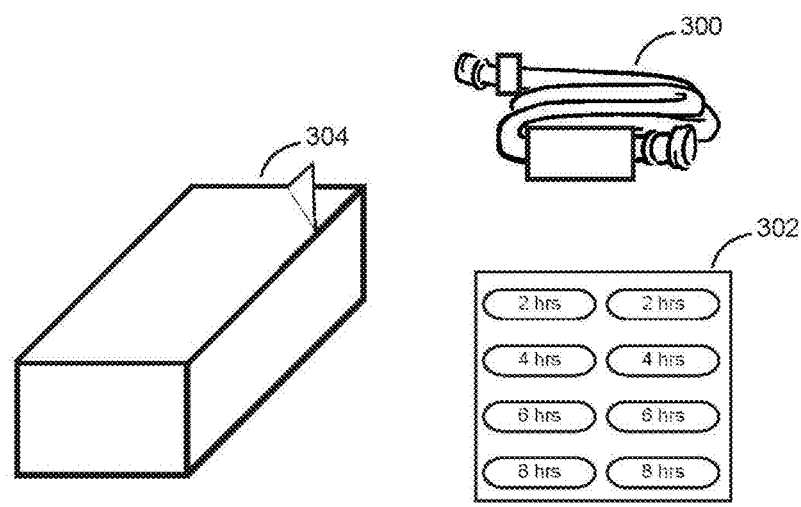
FIG. 3 is a schematic drawing of one embodiment of the present invention showing adhesive interchangeable use protocol indicators for use with a medical device.

FIG. 3 is a schematic drawing of one embodiment of the present invention showing use adhesive protocol indicators for use with a medical device. The medical device 300 and a sheet of adhesive use protocol indicators 302 are packaged together in a sterile environmentally-controlled package 304, for example, carbon dioxide or inert gas. When the user opens the package 304, he or she exposes the adhesive use protocol indicators 302 and the medical device 300 to the intended use environment. The user can then select the adhesive use protocol indicators associated with the use protocol for which he or she intends to use the medical device 300. The selected adhesive use protocol indicators will then change color at the defined time after which the medical device 300 should no longer be used for the particular protocol selected by the user. The color changeable dye can be disposed on or incorporated into the adhesive use protocol indicators.

The present application also involves a method for using interchangeable use protocol indicators. The method involves providing a disposable, limited or restricted use product having more than one use protocol with more than one associated use protocol indicators with the color changeable dye and selecting at least one use protocol indicator.

Another embodiment of the present application deals with providing an exposure time indicator scale that indicates how long a disposable, restricted or limited use product has been exposed to a certain environment and the time remaining before the disposable, restricted or limited use product should no longer be used. In other words, the exposure time indicator reflects a continuum reflecting the time passed and time remaining for the product. Such an apparatus comprises a disposable, limited or restricted use product and an exposure time indicator. The exposure time indicator comprises at least one color changeable dye. The at least one color changeable dye is translucent, milky white or has a first color upon immediate exposure to an environment and the dye changes color after exposure to the environment. The at least one color changeable dye is disposed in such a manner to create a sequential color change that indicates how long the disposable, restricted or limited use product has been exposed to a certain environment and the time remaining before the disposable, limited or restricted use product should no longer be used. The user would not simply know whether a product had reached its expiration date but how long he or she has until it reaches that date.

One example where this might be useful is a feeding tube that should be replaced after approximately one week. A hospital worker could see the exposure time indicator scale and determine when the feeding should be changed. Another example, of the usefulness of the exposure time indicator could be in determining expiration dates on food. Other examples of products where such an indication could prove useful are cosmetic products, personal hygiene products such as electric toothbrush heads, and home diagnostic kits such as pregnancy tests and ovulation prediction tests. In each of these examples, the exposure time indicator allows the user to better plan for change or removal of the product by indicating how long the user has until the product reaches its expiration time.

Figure 4:
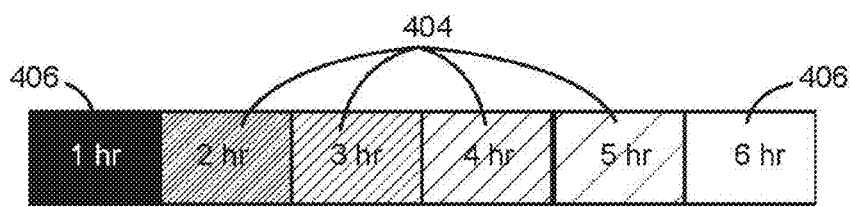
FIG. 4 is a schematic drawing of one embodiment of the present invention showing an exposure time indicator with a color changeable dye that changes color after exposure to an environment in a sequential manner
Figure 5A:
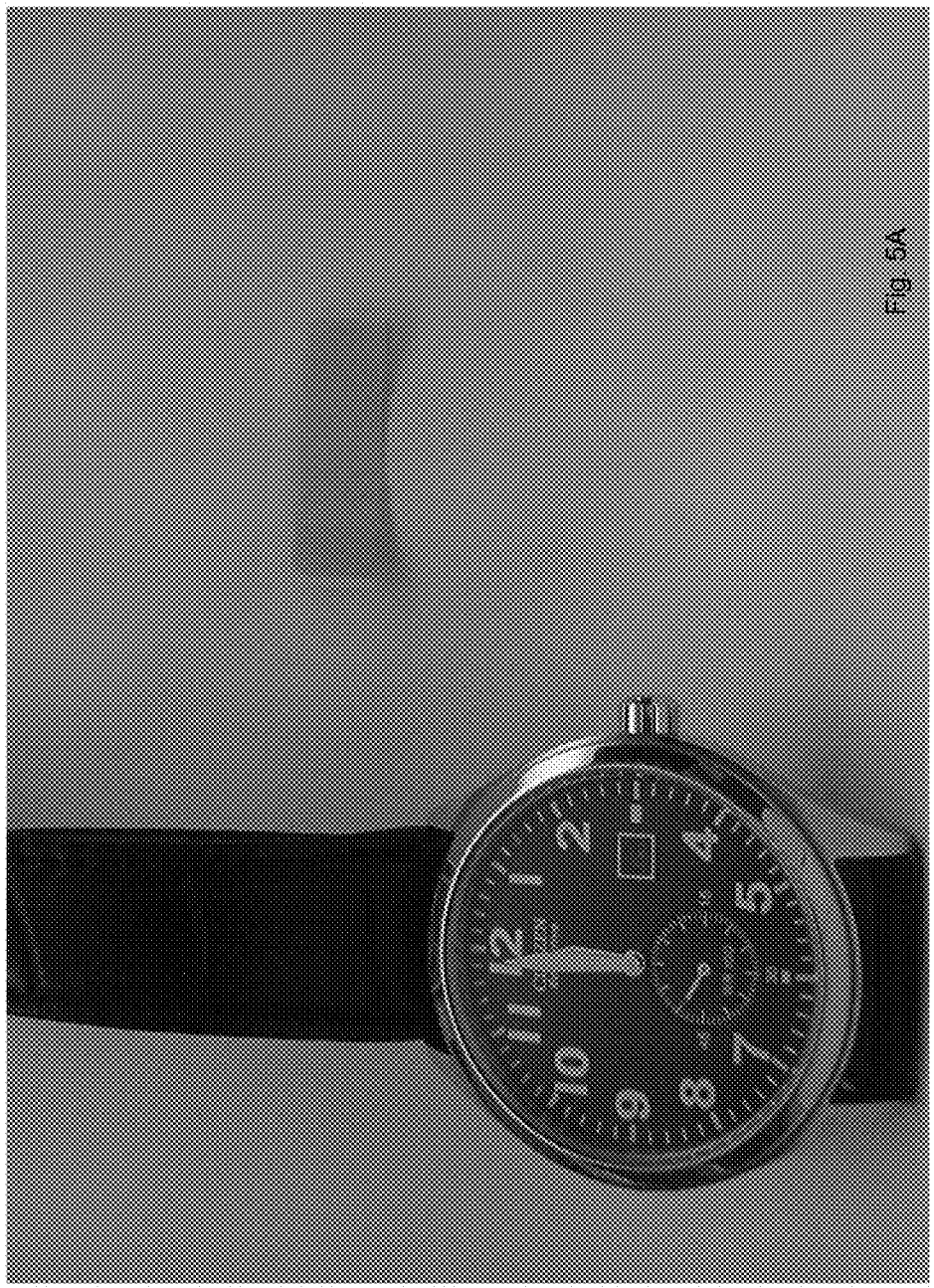
Figure 5C:
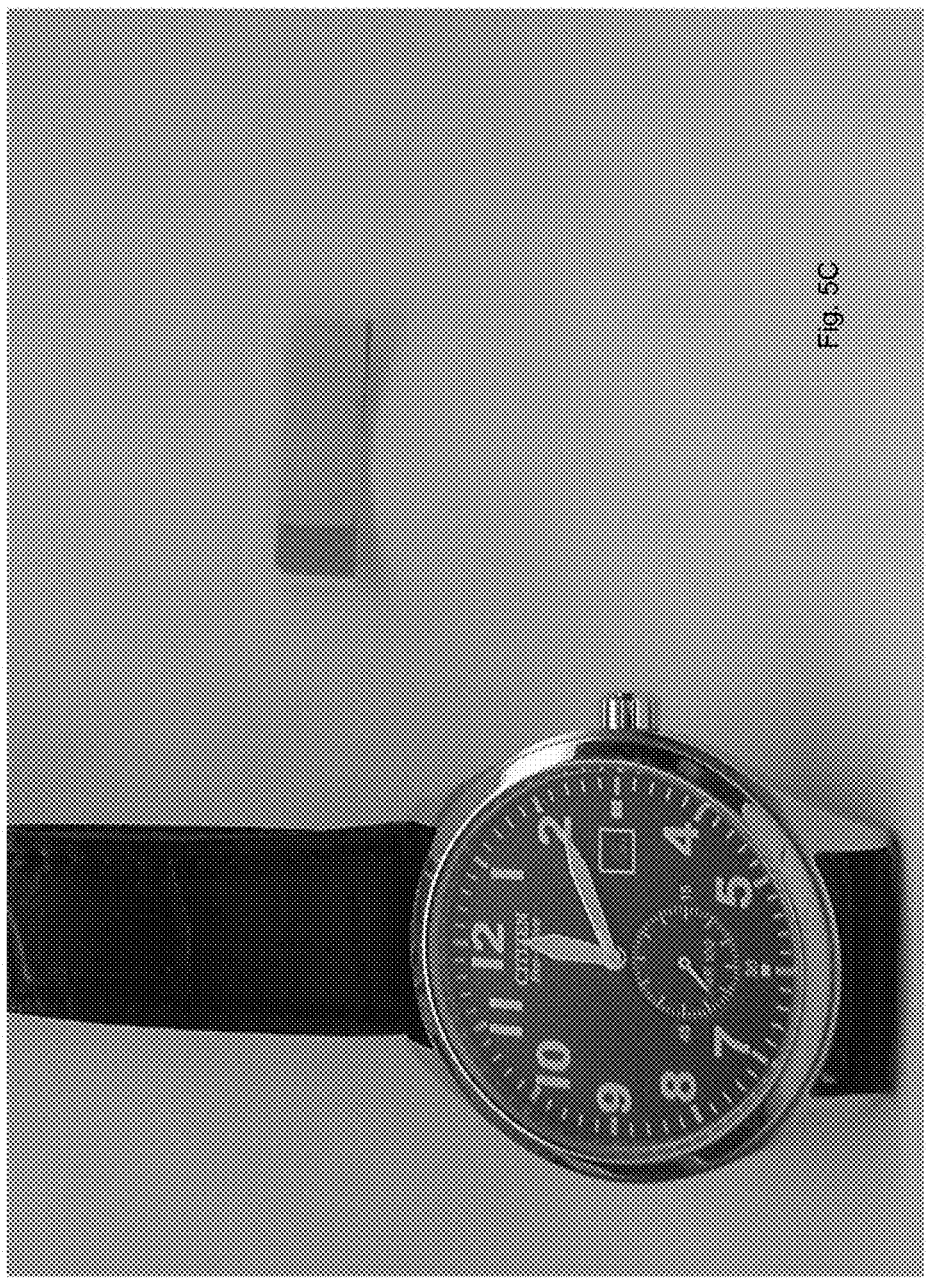
Figure 5D:
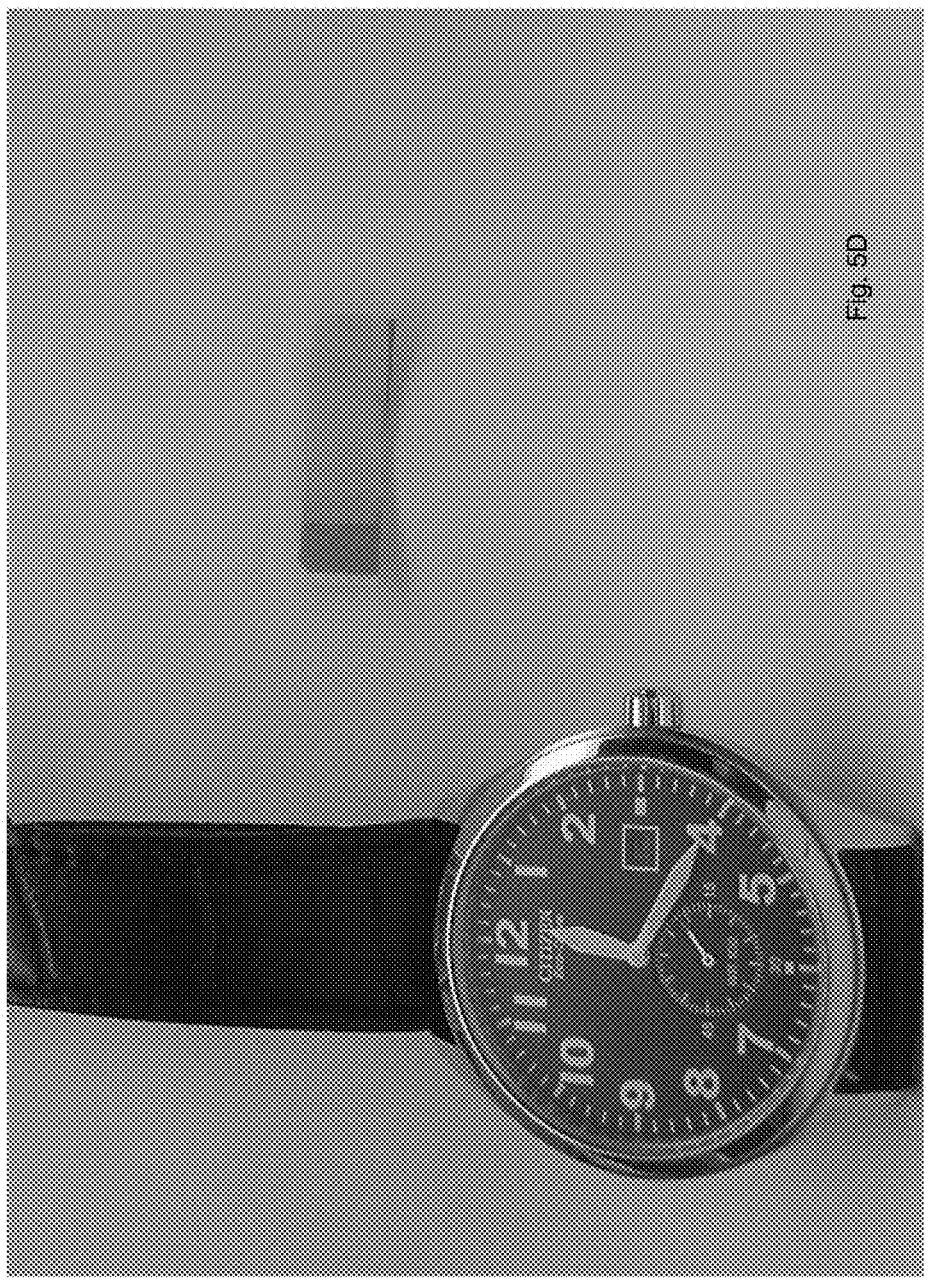
Figure 5F:
Figure 5G:
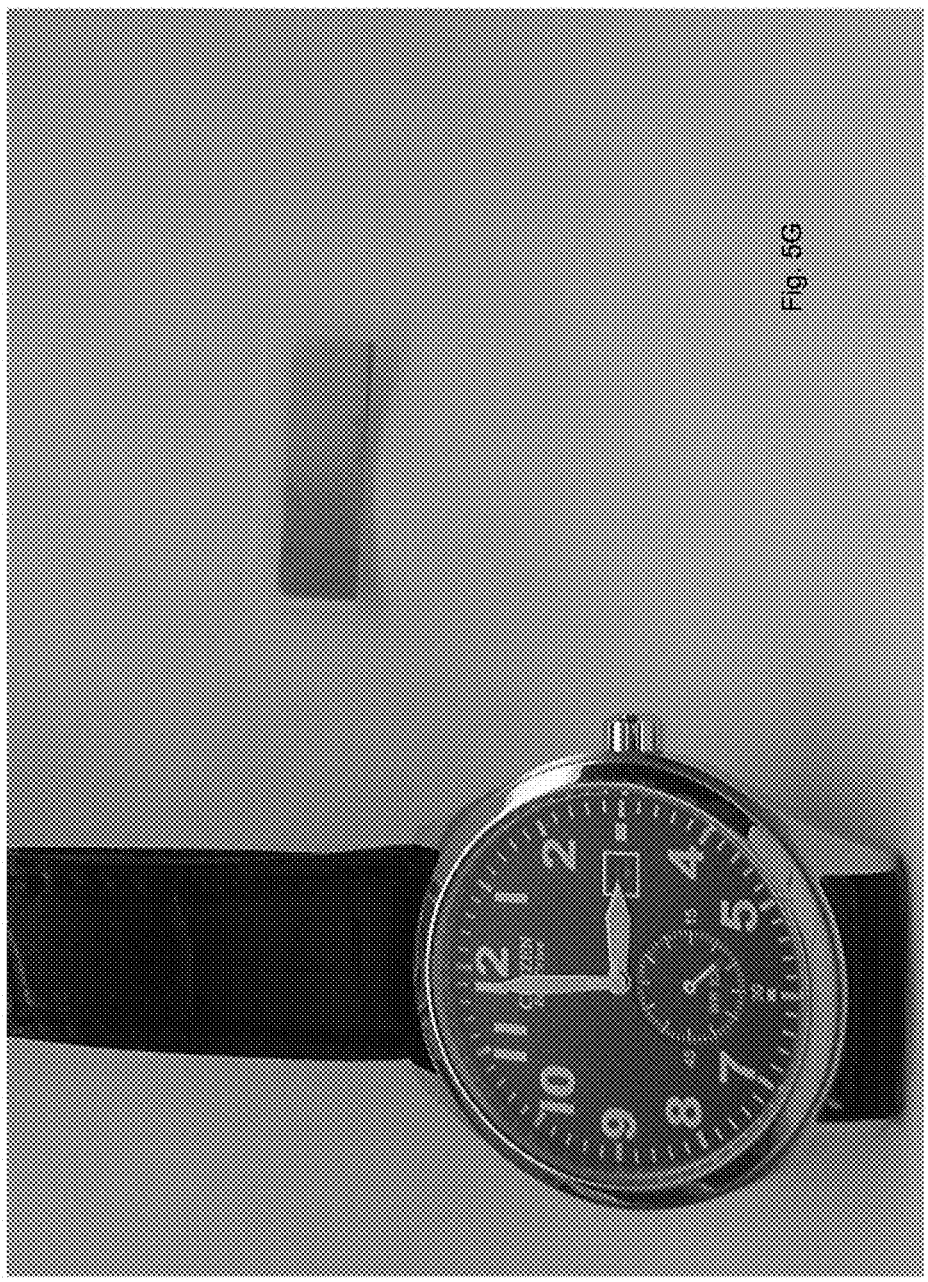
Figure 5H:
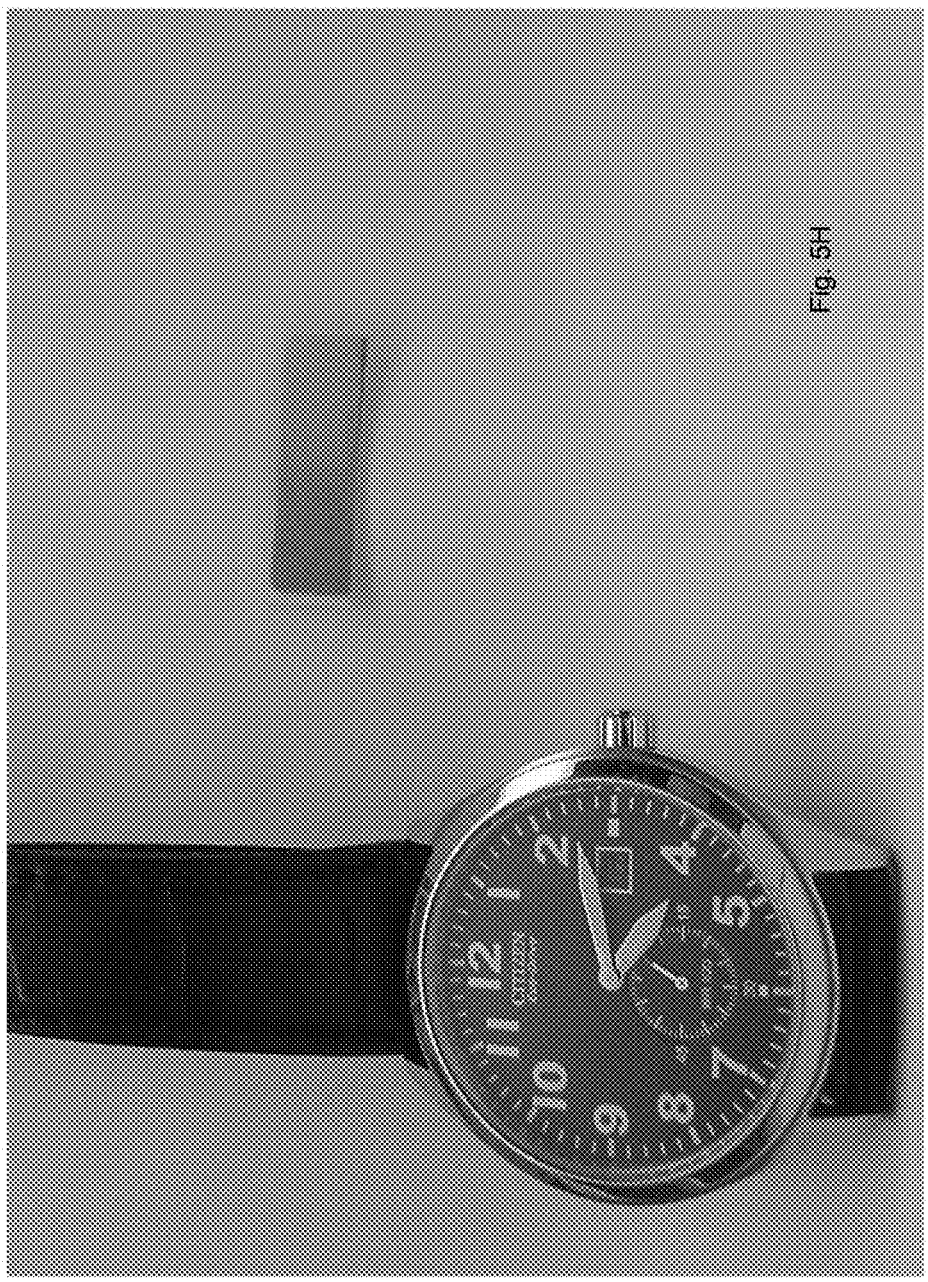
Figure 51:
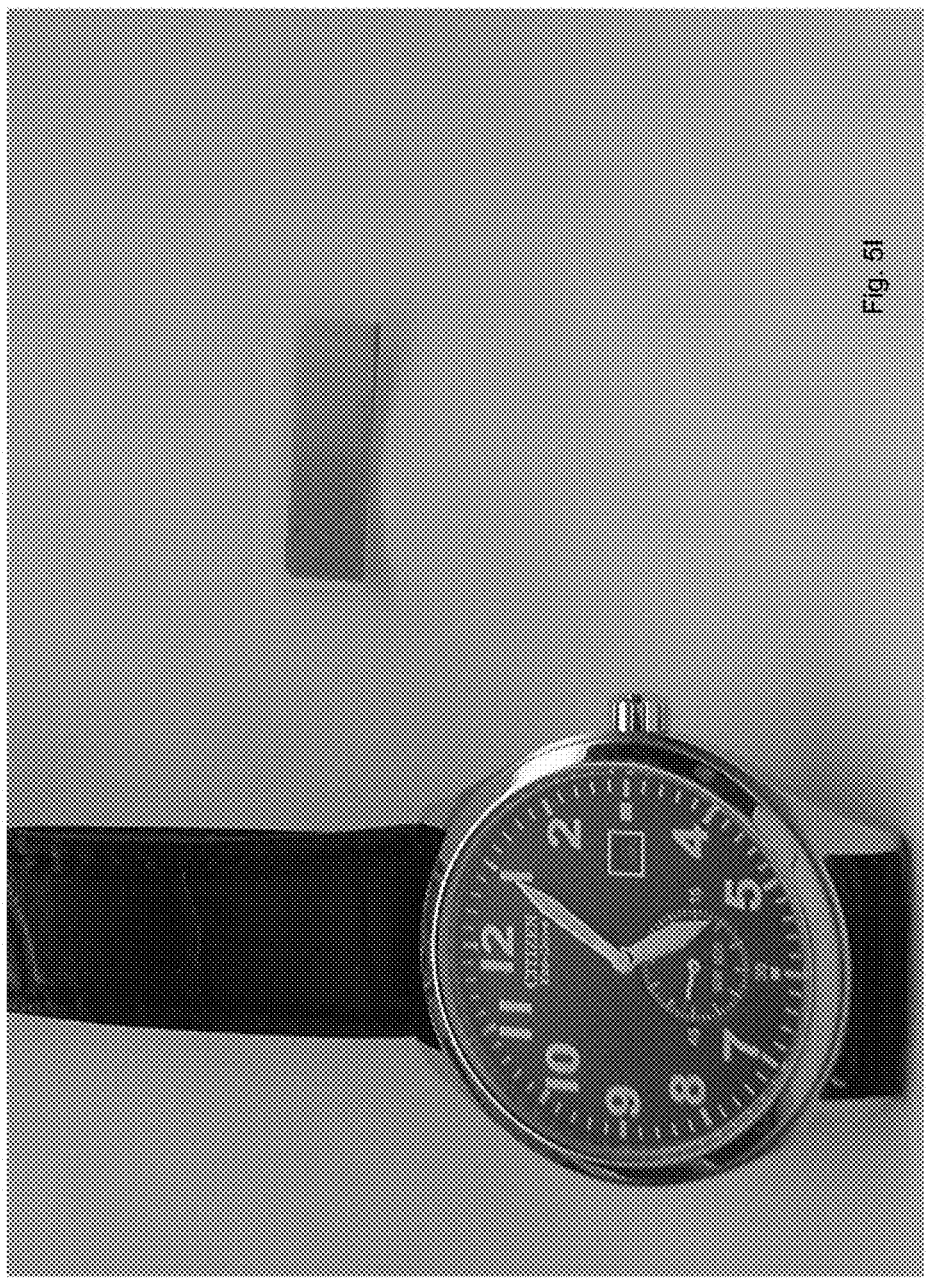
Figure 53:
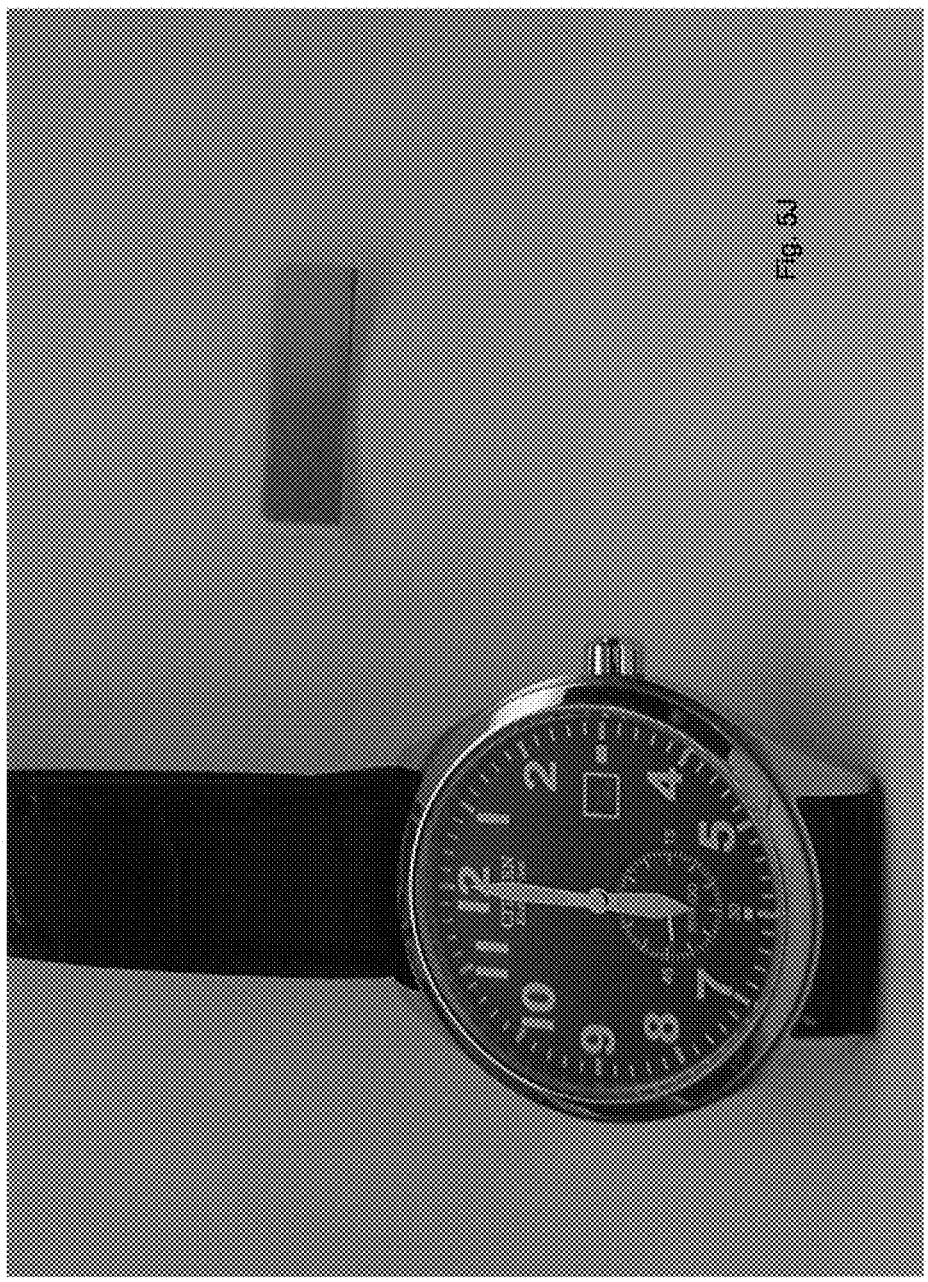
Figure 5K:
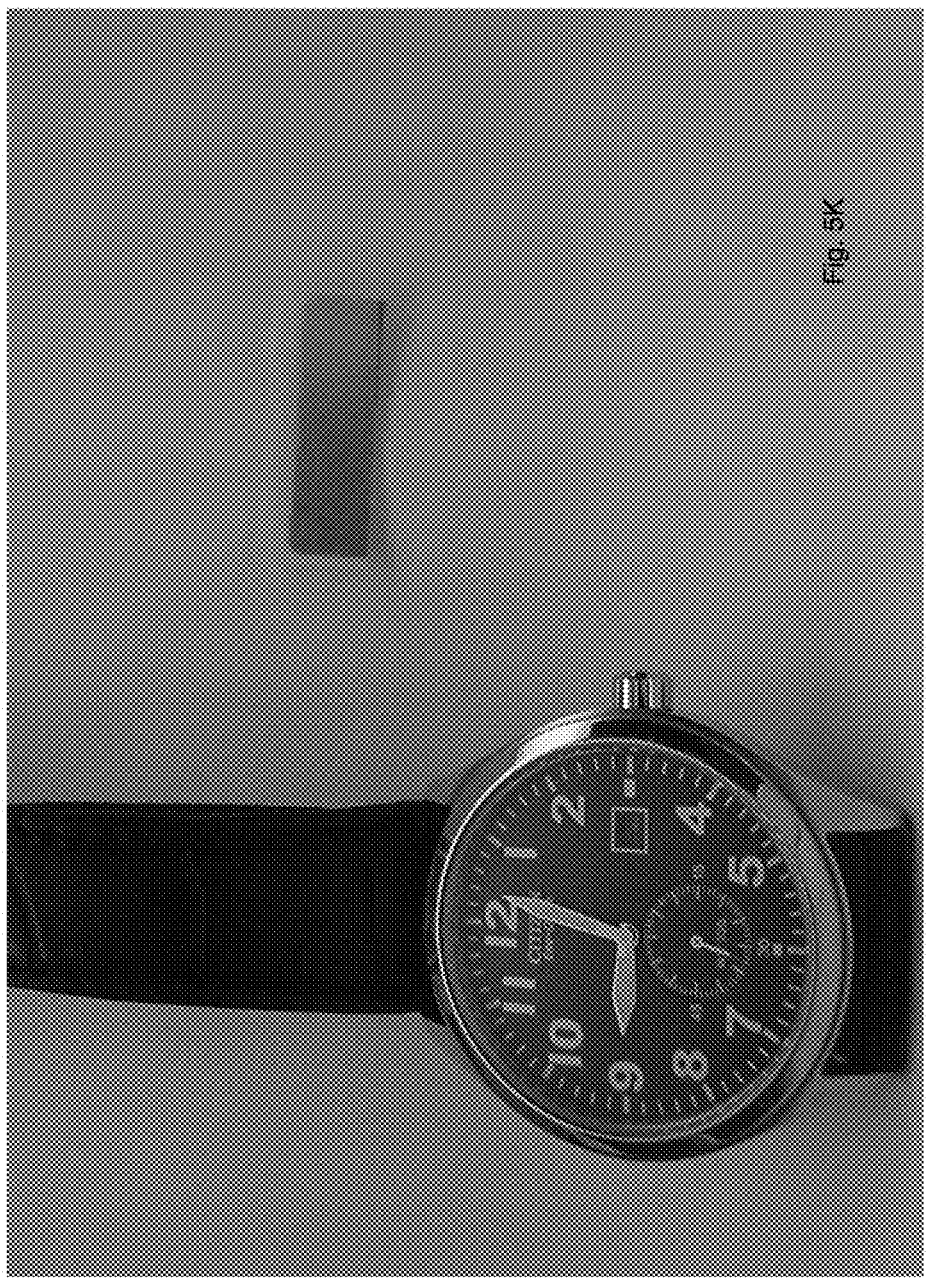
Figure 5L:
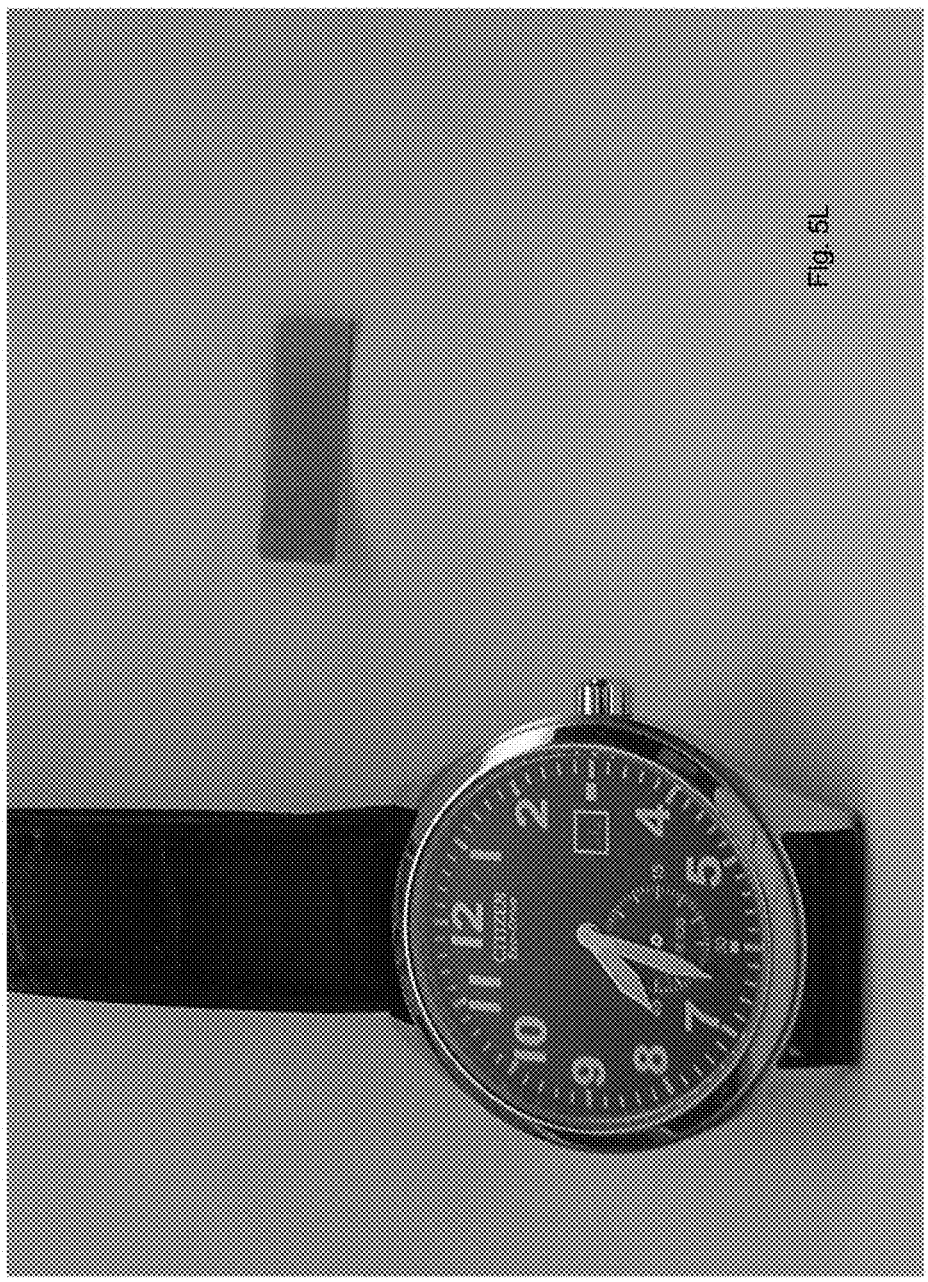

FIG. 4 is a schematic drawing of one embodiment of the present invention showing an exposure time indicator with a color changeable dye that changes color after exposure to an environment in a sequential manner. The exposure time indicator has a first region of a color changeable dye 402 that changes color after a first time, consecutive regions of a color changeable dye 404 that change color at increasing time intervals after the first time and a final region 406 of a color changeable dye that changes color after a final defined time. The final defined time corresponds to a time after which the disposable, limited or restricted use product should not be used.

The color changeable dye can be varied in order to change color in response to a variety of different environments for a defined time for example as discussed above. In a preferred embodiment the environment is an oxygen containing environment and the color changeable dye is an oxygen sensing color changeable dye. In another preferred embodiment the environment is a carbon dioxide containing environment and the color changeable dye is a carbon dioxide sensing color changeable dye. The environment to which the color changeable dye responds can be chosen based on the environment in which the disposable, limited or restricted use product is intended to be used.

In order to create dyes that change color after exposure to different environment after different periods of time there are a number of possible approaches as discussed above. In order to create dyes that change color after exposure to different environment after different periods of time there are a number of possible approaches. Dyes that have completely different compositions can be used. Variations in the makeup of the dye can be used. Scavenger, such as oxygen scavengers, can be added. Barriers can be also be added. Some examples of color changeable dyes using these approaches to achieve color change at different times or in response to different atmospheres were discussed above are equally applicable to this embodiment.

Examples of a color changeable dye that reacts based on carbon dioxide levels in its environment are described above.

Barriers can also be used to achieve the extended sequential color change of the present exposure time indicator. Physical polymer barriers can be applied over the color changeable dye in a stepwise fashion to create a sequential color change. A color changeable dye such as those described above can be disposed onto a substrate, such as a paper indicator strip. Polymer sheets, such as polypropelene, are then disposed on top of the color changeable dye. The polymeric sheets in this can be disposed with no sheets on the first region, one sheet on a second region, two sheets on a third region, three sheets on a fourth region and so on. Single sheets of increasing thickness can also be used.

FIGS. 5A-L are photographs of an exposure time indicator utilizing stepped polymeric barriers with a color changeable carbon dioxide sensing dye (as described above) that changes color in a sequential manner after being removed from a carbon dioxide rich environment and exposed to the intended use environment, e.g., an atmospheric environment. The stepped polymer sheets adhered over the paper indicator strip in the example are 0.002 inch thick cellulose. This device has nine regions with no sheets in the first region, one sheet in the second region, two sheets in the third region and so on. The region with no polymeric strips changes color in a matter of minutes. This can be seen in FIGS. 5A-5D. This rapid change indicates that the test strip is working and has been activated. Each 0.002 inch thick cellulose layer provides about a 2 hour barrier for the color changeable dye. The region with one strip changes color after approximately 2 hours, the region with two strips after approximately 4 hours and so on in a controlled sequential manner. This can be seen in FIGS. 5E-5K. The final region has 8 strips and changes after approximately 16 hours. This can be seen in FIG. 5L. This sequential change allows a user to ascertain the time that has elapsed since the disposable, limited or restricted use product has been opened and to anticipate the remaining time before replacement is required.

More sheets or thicker sheets will extend the indication time. Conversely, fewer sheets or thinner sheets will decrease the indication time. Additionally using a material that has a higher or lower diffusion of gas will also shorten or lengthen the time respectively. For example, Mylar and Teflon have high low diffusion rates for gases and would lengthen the time before color change of the color changeable dye. Polyethylene has a high diffusion rate for gases and would shorten the time before color change of the color changeable dye. Different gases would also diffusion through the barriers at different rates. For example, carbon dioxide is a smaller molecule and would diffuse through more quickly. The time change can further be timed using this information.

The exposure time indicator can be provided in a number of different ways. In one embodiment, the exposure time indicator can be incorporated into the disposable, limited or restricted use product itself. In another embodiment, he exposure time indicator can be disposed directly on the disposable, limited or restricted use product. In another embodiment, the exposure time indicator can also be indirectly disposed on the disposable, limited or restricted use product. For example, the exposure time indicator can be disposed on an adhesive label on the disposable, limited or restricted use product. In yet another, embodiment the exposure time indicator can provided with but separate from the disposable, limited or restricted use product. Alternatively, the exposure time indicator(s) can be provided independently such that a user can use the indicator on a variety of different products.

As discussed above, the exposure time indicator can be incorporated into the disposable, limited or restricted use product. The exposure time indicator can be incorporated into a portion of the disposable, limited or restricted use product and in conjunction with the use protocol indicator described above. In another embodiment, a plastic portion is a multi-layer polymer with the color changeable dye incorporated therein.

In yet another embodiment a component has a capillary with the color changeable dye incorporated therein. As described above, FIG. 2 is a schematic drawing of one embodiment of the present invention where the exposure time indicator could be used. Specifically, the color change can be controlled to proceed in a sequential manner using the exposure time indicator. The color change can move in a continuum around the capillary in a sequential manner through a first region, consecutive regions and a final region to indicate the time passed and time until which the disposable, limited or restricted use product should no longer be used. Moreover, additional barrier materials may be incorporated into the capillary to further delay the color change of the dye.

While the application has been described with reference to certain embodiments, it will be understood by those skilled in the art that various changes may be made and equivalents may be substituted without departing from the scope of the application. In addition, many modifications may be made to adapt a particular situation or material to the teachings of the application without departing from its scope. Therefore, it is intended that the application not be limited to the particular embodiment disclosed, but that the application will include all embodiments falling within the scope of the appended claims.

The invention claimed is:

1. An apparatus with color change indication comprising:
a disposable, limited or restricted use product having more than one use protocol;
a first interchangeable color change indicator having a first color changeable dye, the dye having an initial color upon immediate exposure to an environment and the dye changing color after exposure to the environment for a first defined time;
a second interchangeable color change indicator having a second color changeable dye, the dye having an initial color upon immediate exposure to the environment and the dye changing color after exposure to the environment for a second defined time different than the first defined time; and
wherein the first defined time corresponds to an expiration time for a first use protocol and the second defined time corresponds to an expiration time for a second use protocol.

2. The apparatus of claim 1 wherein said environment is an oxygen containing environment and said first and second color changeable dyes are oxygen sensing color changeable dyes.

3. The apparatus of claim 1 wherein said environment is a carbon dioxide containing environment and said first and second color changeable dyes are carbon dioxide sensing color changeable dyes.

4. The apparatus of claim 1 wherein said environment is a carbon dioxide containing environment and said first and second color changeable dyes are oxygen sensing color changeable dyes.

5. The apparatus of claim 1 wherein at least one interchangeable color change indicator is incorporated into the disposable, limited or restricted use product.

6. The apparatus of claim 1 wherein at least one interchangeable color change indicator is disposed on the disposable, limited or restricted use product.

7. The apparatus of claim 1 wherein at least one interchangeable color change indicator is an exposure time indicator.

8. The apparatus of claim 1 wherein at least one interchangeable color change indicator has a capillary with the color changeable dye incorporated therein.

9. The apparatus of claim 1 wherein the first and second color change indicators are provided with the disposable, limited or restricted use product.

10. The apparatus of claim 1 wherein the initial color of the first color changeable dye is translucent and wherein the initial color of the second color changeable dye is translucent.

11. The apparatus of claim 1 wherein the product is a medical device.

12. An apparatus having a color change indicator comprising:
a first color changeable dye, the dye having a first color in a first environment and the dye configured to change to a second color after immediate exposure to a second environment;
a second color changeable dye, the dye having a first color in the first environment and upon immediate exposure to the second environment and for a defined time thereafter and the dye configured to change color to a second color after exposure to the second environment for a defined time.

13. The apparatus of claim 12 wherein the first environment is selected from the group consisting of carbon dioxide or inert gas and the second environment is atmospheric oxygen.

14. The apparatus of claim 12 wherein the indicator comprises an exposure time indicator.

15. The apparatus of claim 12 wherein the first color of the first color changeable dye is translucent and wherein the first color of the second color changeable dye is translucent.

16. A method of using an apparatus with color change indication comprising:
providing a disposable, limited or restricted use product having at least two use protocols;
selecting at least one color change indicator from a group of at least two color change indicators for use with the disposable, limited or restricted use product,
the at least two color change indicators each having a color changeable dye that has an initial color upon immediate exposure to an environment and changes color after exposure to the environment for a defined time
wherein the defined times of the at least two color change indicators are different and each defined time corresponds with expiration times of the at least two use protocols.

17. The method of claim 16 wherein the initial color of at least one of the color changeable dyes is translucent.

18. A kit comprising:
more than one interchangeable color change indicator, each indicator having a color changeable dye, the dye having an initial color upon immediate exposure to an environment and the dye changing color after exposure to the environment for a defined time
wherein said more than one color change indicators have different defined times corresponding to an expiration time for a use protocol.

19. The kit of claim 18 wherein the kit further comprises a disposable, limited or restricted use product.

20. The kit of claim 19 wherein the product is a medical device.

21. The kit of claim 18 wherein the color change indicators are adhesive use protocol indicators.

22. The kit of claim 18 wherein the initial color of the dye is translucent.

* * * * *